United States Patent [19]

Fenyes et al.

[11] 3,932,478
[45] Jan. 13, 1976

[54] PHOSPHONIC ACID HALF-ESTERS AND THEIR DERIVATIVES

[75] Inventors: Joseph G. E. Fenyes; Kenneth J. Flanagan, both of Memphis, Tenn.

[73] Assignee: Buckman Laboratories, Inc., Memphis, Tenn.

[22] Filed: Oct. 3, 1973

[21] Appl. No.: 399,023

Related U.S. Application Data

[60] Division of Ser. No. 168,744, Aug. 3, 1971, abandoned, which is a continuation-in-part of Ser. No. 127,776, March 24, 1971, Pat. No. 3,767,735.

[52] U.S. Cl. .............. 260/429.7; 44/68; 44/DIG. 4; 106/15 FP; 252/8.1; 252/49.7; 252/49.8; 252/400; 260/45.75 R; 260/45.75 K; 260/45.75 N; 260/429.9; 260/439 R; 260/448 R
[51] Int. Cl.$^2$ ........................................... C07F 7/22
[58] Field of Search .......... 260/429.7, 429.9, 439 R, 260/429, 448 R

[56] References Cited
UNITED STATES PATENTS

| | | | |
|---|---|---|---|
| 3,423,487 | 1/1969 | Scheuerer et al. | 260/946 |
| 3,696,135 | 10/1972 | Kartschmaroff | 260/439 R |
| 3,754,019 | 8/1973 | Sarett et al. | 260/448 R X |
| 3,767,735 | 10/1973 | Fenyes et al. | 260/448 R X |
| 3,824,192 | 7/1974 | Di Battista | 260/45.75 V X |

*Primary Examiner*—Helen M. S. Sneed
*Attorney, Agent, or Firm*—Floyd E. Trimble

[57] ABSTRACT

Unsubstituted and substituted dialkyl esters of phosphoric and diphosphonic acids, nuclearly brominated derivatives thereof, and metal mono-, bis-, and trisderivatives of phosphonic acid half-esters are useful as ultraviolet light absorbers and as fire retardants.

9 Claims, No Drawings

PHOSPHONIC ACID HALF-ESTERS AND THEIR DERIVATIVES

This is a division of application Ser. No 168,744 filed Aug. 3, 1971, abandoned, which is a continuation-in-part of application Ser. No. 127,776 filed Mar. 24, 1971, U.S. Pat. No. 3, 767,735 dated Oct. 23, 1973.

This invention relates to novel derivatives of phosphonic and diphosphonic acids, their preparation and use as ultraviolet light absorbers and as fire retardants. More particularly, the present invention relates to the preparation and use of the novel compounds of our invention which may be defined as phosphonic acid derivatives selected from the class consisting of unsubstituted and substituted dialkyl esters of phosphonic and diphosphonic acids, nuclearly brominated derivatives thereof, and metal mono-, bis-, and tris-[(O-alkyl)-3-acetyl-4-hydroxybenzyl]phosphonates.

It is well known that many organic compositions such as polymeric organic compositions tend to undergo deterioration when exposed to ultraviolet light. Light in the ultraviolet portion of the spectrum and particularly that having a wavelength within 290–400 millimicrons causes photocatalyzed changes, such as yellowing and/or embrittlement of unstabilized polymeric compositions. These changes are obviously undesirable and this is particularly true when the composition is initially colorless, transparent, or translucent and is to be used subsequently under conditions that will subject it to long exposure to sunlight or other sources of ultraviolet light radiation. Examples of such applications include translucent roofing materials, transparent structures, decorative structures, decorative and protective coatings, and impact-resistant windows.

In recent years, many organic compounds have become available which can absorb ultraviolet light and convert it to less harmful forms of energy such as heat, vibrational energy, or less harmful radiation. These organic stabilizers, in addition to absorbing ultraviolet radiation in the selected range for the polymeric compositions being treated, must be compatible therewith, have little or no initial color, be reasonably inexpensive, be chemically stable, and have a low toxicity, especially for stabilizing compositions to be used subsequently in the food industry.

A good ultraviolet absorber for use in polymeric organic compositions should absorb the ultraviolet radiation in daylight, impart no or very little color to the composition, should be sufficiently stable to withstand curing conditions, and should absorb ultraviolet light sufficiently to protect the composition against yellowing and decomposition on exposure to ultraviolet light. The compound must have sufficient solubility in various types of materials so that it may be incorporated therein, it should be capable of withstanding leaching action of solvents or loss by exudation.

Generally, an effective ultraviolet absorber should have its peak absorption above a wavelength of 300 millimicrons or the absorption peak may be at a higher wavelength as long as the absorption drops off sufficiently as it approaches the visual range so that no color is visible. In addition, to be effective it should show a high degree of absorbancy in the desired wavelength range, especially at those wavelengths sufficiently below the visual range so that the compound has no yellow color.

Although, as pointed out above, many compounds have been suggested for the stabilization of polymeric organic compositions against deterioration caused by ultraviolet light none have been entirely satisfactory as all have been deficient in one or more qualities which the ideal ultraviolet absorber must possess. These include, in addition to lack of color, the ability to become firmly incorporated in the composition to be stabilized and the ability to absorb ultraviolet light over a wide range. The latter is important because individual polymeric organic compositions are generally most susceptible to deterioration by radiation of a specific wavelength. For example, polyethylene, polypropylene, and polystyrene are susceptible to radiation wavelengths of 300–320 millimicrons. Many of the absorbers disclosed in the prior art exhibit excellent ultraviolet light absorption only over a very limited wavelength. Another criteria of a polymeric organic composition in addition to its resistance to deterioration on exposure to ultraviolet light is that it be as resistant to fire as possible.

Heretofore when it was necessary to protect polymeric organic compositions against deterioration caused by exposure to ultraviolet light and to impart fire retardant properties to the composition, the use of two additives was mandatory; one to protect the composition against ultraviolet light and the other to attain the desired fire-retardant properties. This is objectionable because when two additives are used, each must not only perform its particular function effectively, but, in addition, the two must be compatible. Obviously, a single compound effective both as an ultraviolet light absorber and as a fire-retardant would eliminate completely the compatibility requirement and for that reason be desirable.

It is, therefore, a principal object of the present invention to provide an additive for polymeric organic compositions which is effective as an ultraviolet light absorber and is capable of rendering such compositions fireretardant.

It is another object of our invention to provide a composition which is resistant to degradation by ultraviolet light radiation and is fire resistant.

These and other objects and advantages will become apparent as the description proceeds.

To the accomplishment of the foregoing and related ends, this invention then comprises the features hereinafter fully described and particularly pointed out in the claims, the following description setting forth in detail certain illustrative embodiments of the invention, these being indicative, however, of but a few of the various ways in which the principles of the invention may be employed.

In brief, the foregoing objects and advantages are obtained by incorporating into a polymeric organic composition susceptible to deterioration by the action of ultraviolet light radiation a compound identified generically as unsubstituted and substituted dialkyl esters of phosphonic and diphosphonic acids, nuclearly brominated derivatives thereof, and metal mono-, bis-, and tris-[(O-alkyl)-3-acetyl-4-hydroxybenzyl]phosphonates in an amount varying from 0.1 to 5.0 percent by weight based on the total weight of the polymeric organic composition. When the compounds of our invention are employed as a fire retardant, the amount used may vary from 1 to 15 percent. It is understood, of course, the larger quantities of the phosphonate may be used, but such is not generally desirable because costs may be increased thereby without commensurate additional beneficial results.

Alternately, these ultraviolet light absorbers and fire retardants may be identified as compounds having the formula:

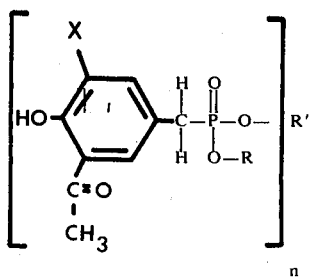

wherein R is a straight or branched chain alkyl radical containing from 1 to 18 carbon atoms. This alkyl group may be unsubstituted or substituted wherein the substituent is a halogen. R' is an alkyl radical as defined for R with the further provision that R' may also represent a metal having a valence of 1 to 3, n is an integer varying from 1 to 3, and X is bromine, hydrogen, methylene dialkyl phosphonate, or methylene bis-beta-chloroethyl phosphonate. Alternately, the latter group may be represented by the radical

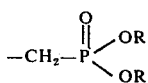

wherein R is as identified above.

Polymeric organic compositions which can be protected from the degrading effects of ultraviolet light and fire by the use of the compositions of our invention include alkyd resins as disclosed in U.S. Pat. Nos. 1,847,783, 1,860,164, 1,950,468, and 2,087,852; epoxy resins as disclosed in U.S. Pat. No. 2,886,473; polyester resins; polyurethane; polyethylene; polypropylene; polystyrene; polyvinyl chloride resins; cellulosic and acrylic polymers; linear super polyamide obtained by condensing an aliphatic polyethylenediamine with a dicarboxylic acid; industrial coatings including decorative and protective coatings wherein one or more of the components thereof comprises an organic composition susceptible to deterioration when exposed to ultraviolet light and/or coated fabrics such as fabrics coated with polyvinyl chloride and polyolefin; and polyvinylidene chloride monofilaments.

In order to disclose the nature of the invention still more clearly, the following illustrative examples will be given. It is understood, however, that the invention is not to be limited to the specific conditions or details set forth in these examples, except insofar as such limitations are specified in the appended claims.

In the examples, "parts" where used are parts by weight.

EXAMPLE 1

Di-(n-butyl)-3-acetyl-4-hydroxybenzyl phosphonate

A one-liter, four neck, round-bottom flask equipped with stirrer, condenser, thermometer, and gas inlet was charged with 75.0 grams (0.3 mole) of tri(n-butyl)-phosphite and 55.4 grams (0.3 mole) of 5'-chloromethyl-2'-hydroxyacetophenone. The mixture was purged for 5 minutes with nitrogen while stirring and then gently heated to 65°–70°C., at which point exothermicity set in and butyl chloride distilled at about 76° to 79°C. The mixture was then heated to approximately 100°–110° at atmospheric pressure to complete the distillation ot butyl chloride and then distilled under vacuum to yield the product de-(n-butyl)-3-acetyl-4-hydroxybenzyl phosphonate, b.p. 155°C./0.15 mm.

EXAMPLE 2

Sodium [(0-butyl)-3-acetyl-4-hydroxybenzyl]phosphonate

A one-liter, four neck, round-bottom flask equipped with stirrer, reflux condenser, thermometer, and gas inlet was charged with 75.0 grams (0.215 mole) of di-(n-butyl)-3-acetyl-4-hydroxybenzyl phosphonate prepared in Example 1, to which was then added 34.4 grams of a 50 percent aqueous sodium hydroxide solution in 32.5 milliliters of methanol under nitrogen. After five minutes of purging with nitrogen, the nitrogen stream was stopped and the reaction mixture was refluxed 4.5 hours, after which time it was cooled to room temperature and neutralized with concentrated HCl to pH 76 with cooling. The precipitated sodium chloride was removed by filtration and washed with a small amount of isopropyl alcohol. The washing and filtrate were combined and concentrated under reduced pressure. The dry residue was dissolved in a small amount of methyl alcohol and the insoluble solids, identified as sodium chloride, were removed by filtration. The filtrate was evaporated in vacuo to dryness, m.p. 193°–195°C. This product was used without any further purification for the preparation of nickel and tin salts.

EXAMPLE 3

Preparation of nickel bis-[(0-butyl)-3-acetyl-4-hydroxybenzyl]phosphonate

A one-liter, three neck, round-bottom flask equipped with stirrer, reflux condenser, and thermometer was charged with 9.2 grams (0.029 mole) of sodium [(0-butyl)-3-acetyl-4-hydroxybenzyl]phosphonate prepared in Example 2 dissolved in 100 milliliters of methanol to which was then added 3.6 grams (0.015 mole) of nickelous chloride hexahydrate dissolved in 20 milliliters of methanol. The reaction mixture w as stirred and heated at reflux for a period of one hour, after which it was filtered and the filtrate evaporated to dryness under vacuum. The pale green product did not melt up to 300°C. Anal. calculated for $C_{26}H_{36}NiO_{10}P_2$: P, 9.84 percent; Ni, 9.33 percent. Found: P, 9.68 percent; Ni, 9.13 percent.

EXAMPLE 4

Diethyl-3-acetyl-4-hydroxybenzyl phosphonate

The foregoing compound was prepared following the same experimental procedure as used in Example 1. In this example, 92.3 grams (0.5 mole) of 5'-chloromethyl-2'-hydroxyacetophenone was reacted with 83.0 grams (0.5 mole) of triethyl phosphite. The crude yellow product obtained was purified by distillation. The colorless liquid obtained as a distillate and identified by its infrared spectrum as diethyl-3-acetyl-4-hydroxybenzyl phosphonate weighed 111.5 grams. This represented a yield of 77.9 percent of theory.

If desired, the reaction may be carried out in the presence of an inert solvent such as benzene, toluene, xylene, or chloroform. This modification of the experimental procedure lessens the vigor of the reaction.

EXAMPLE 5

Sodium [(0-ethyl)-3-acetyl-4-hydroxybenzyl]phosphonate

The foregoing compound was prepared following the same experimental procedure as used in Example 2. In this example, the product of Example 4 (111.5 grams) was reacted with 62.4 grams of a 50 percent aqueous sodium hydroxide solution to produce 68.0 grams of an off-white product identified as crude sodium [(0-ethyl)-3-acetyl-4-hydroxybenzyl]phosphonate. This product had a melting point of 210°–220°C. and represented a yield of 62.4 percent of theory.

EXAMPLE 6

Nickel bis-[(0-ethyl)-3-acetyl-4-hydroxybenzyl]phosphonate

The same experimental procedure as that used in Example 3 was used, in which 14.0 grams (0.05 mole) of sodium [(0-ethyl-3-acetyl-4-hydroxybenzyl]phosphonate was reacted with 6.0 grams (0.025 mole) of nickelous chloride hexahydrate. A pale green compound weighing 8.2 grams (57.4 percent) and having a melting point higher than 300° C. was obtained. Anal. calculated for $C_{22}H_{26}NiO_{10}P$: P, 10.81 percent; Ni, 10.24 percent. Found: P, 9.58 percent, Ni, 9.19 percent.

EXAMPLE 7

Di(isopropyl)-3-acetyl-4-hydroxybenzyl phosphonate

The same experimental procedure as used in Examples 1 and 4 was used. In this example, 92.3 grams (0.5 mole) of 5'-chloromethyl-2'-hydroxyacetophenone was reacted with 104.1 grams (0.5 mole) of triisopropyl phosphite. The reaction can also be carried out in an inert solvent such as benzene, toluene, xylene, or chlorobenzene to moderate the vigor of the reaction. The crude product, 142 grams (90.6 percent) was used in Example 8 without any further purification.

EXAMPLE 8

Sodium (0-isopropyl-3-acetyl-4-hydroxybenzyl)phosphonate

The same experimental procedure as used in Examples 2 and 5 was used. In this example, 157.1 grams (0.5 mole) of di(isopropyl)-3-acetyl-4-hydroxybenzyl phosphonate was used with 80.0 grams of 50 percent aqueous NaOH. The crude sodium (0-isopropyl-3-acetyl-4-hydroxybenzyl)phosphonate so obtained weighed 139 grams, representing a yield of 94.5 percent of theory.

EXAMPLE 9

Nickel bis-[(0-isopropyl)-3-acetyl-4-hydroxybenzyl]phosphonate

The same experimental procedure of Examples 3 and 6 was followed. In this example, 147.1 grams (0.5 mole) of sodium (0-isopropyl-3-acetyl-4-hydroxybenzyl) phosphonate in 350 milliliters of methanol was treated with 59.4 grams (0.25 mole) of nickelous chloride hexahydrate in 150 milliliters of methanol. The reaction mixture was filtered to remove sodium chloride and the green-colored filtrate was evaporated to dryness under diminished pressure to give a pale green residue weighing 110 grams (73.5 percent yield) which was identified by characteristics peaks in its infrared spectrum as nickel bis-(0-isopropyl)3-acetyl-4-hydroxybenzyl)phosphonate, m.p. > 300°C.

EXAMPLE 10

Di(isooctyl)-3-acetyl-4-hydroxybenzyl phosphonate

In this example the experimental procedure of Examples 1, 4, and 7 was followed. Forty-six and one tenth grams of 5'-chloromethyl-2'-hydroxyacetophenone (0.25 mole) was treated with 104.6 grams (0.25 mole) of triisooctyl phosphite. After the reaction was completed, the crude di(isooctyl)-3-acetyl-4-hydroxybenzyl phosphonate was used directly without further purification for the preparation of the sodium salt of the corresponding half-ester.

EXAMPLE 11

Sodium(0-isooctyl-3-acetyl-4-hydroxybenzyl)phosphonate

The same experimental procedure as used in Examples 2, 5, and 8 was used to treat 114 grams (0.25 mole) of di(isooctyl-3-acetyl-4-hydroxybenzyl phosphonate in 100 milliliters of methanol with 40 grams of 50 percent aqueous sodium hydroxide to give 77 grams (84.5 percent yield) of sodium (0-isooctyl-3-acetyl-4-hydroxybenzyl)phosphonate. This compound was identified by spectroscopic method.

EXAMPLE 12

Nickel bis-[(0-isooctyl)-3-acetyl-4-hydroxybenzyl]phosphonate

The same experimental procedure as used in Examples 3, 6, and 9 was used to react 91.1 grams (0.25 mole) of sodium (0-isooctyl-3-acetyl-4-hydroxybenzyl)-phosphonate with 29.7 grams (0.25 mole) of nickelous chloride hexahydrate. Eighty-three grams (90 percent yield) of nickel bis-[(0-isooctyl)-3-acetyl-4-hydroxybenzyl]phosphonate was obtained, m.p. > 300°C.

EXAMPLE 13

Dimethyl-3-acetyl-4-hydroxybenzyl phosphonate

The same experimental procedure as that used in Examples 1, 4, 7, and 10 was used to treat 184.6 grams (1.0 mole)of 5'-chloromethyl-2'-hydroxyacetophenone with 124 grams (1.0 mole) of trimethyl phosphite. This reaction was the most vigorous of all the reactions aimed at the preparation of a dialkyl-3-acetyl-4-hydroxybenzyl phosphonate. The reaction can be moderated by cooling once the evolution of methyl chloride is started. Alternately and somewhat preferably, the reaction may be carried out in an inert solvent such as benzene, toluene, xylene, or chlorobenzene. The product (240 grams, 93 percent) was identified by its characteristic infrared bands as dimethyl-3-acetyl-4-hydroxybenzyl phosphonate and was used without any further purification in the next reaction.

EXAMPLE 14

Sodium [(0-methyl)-3-acetyl-4-hydroxybenzyl]phosphonate

The same experimental procedure as that used in Examples 2, 5, 8, and 11 was used to treat 240 grams (0.93 mole) of dimethyl-3-acetyl-4-hydroxybenzyl phosphonate with 148.8 grams of 50 percent aqueous sodium hydroxide. One hundred and sixty-four grams (69 percent yield) of a dark brown compound was obtained, m.p. 200°–210°C.

EXAMPLE 15

Nickel bis-[(0-methyl)-3-acetyl-4-hydroxybenzyl]phosphonate

The same experimental procedure as that used in Examples 3, 6, 9, and 12 was used to react 48.5 grams (0.182 mole) of sodium [(0-methyl)-3-acetyl-4-hydroxybenzyl]phosphonate with 21.6 grams (0.091 mole) of nickelous chloride hexahydrate. A green powdery product weighing 43 grams (87.4 percent yield) was obtained and was identified by its infrared spectrum as nickel bis-[(0-methyl)-3-acetyl-4-hydroxybenzyl]phosphonate, m.p. >300°C.

EXAMPLE 16

Aluminum tris-[(0-ethyl)-3-acetyl-4-hydroxybenzyl]phosphonate

A 500-milliliter, three neck, round-bottom flask was charged with 29.7 grams (0.105 mole) of sodium [(0-ethyl)-3-acetyl-4-hydroxybenzyl]phosphonate, 250 milliliters of methanol, and 8.5 grams (0.0353 mole) of aluminum chloride hexadrate in 100 milliliters of methanol. The stirred mixture was heated at reflux temperature for 1 hour. After cooling to room temperature, the white precipitate formed was collected on a Buchner funnel, washed with water and air dried to give 23.5 grams (82.8 percent yield) of a white compound which was characterized by its infrared spectrum as aluminum tris-[(0-ethyl)-3-acetyl-4-hydroxybenzyl]phosphonate, m.p. > 300°C.

EXAMPLE 17

Zinc bis-[(0-ethyl)-3-acetyl-4-hydroxybenzyl]phosphonate

The same experimental procedure as that used in Example 16 was used to treat a suspension of 28 grams (0.1 mole) of sodium [(0-ethyl)-3-acetyl-4-hydroxybenzyl]phosphonate in 175 milliliters of methanol with a suspension of 6.8 grams (0.05 mole) of zinc chloride in approximately 50 milliliters of methanol. Twenty-five grams (86 percent yield) of a white powdery material was obtained and was spectroscopically identified as zinc bis-[(0-ethyl)-3-acetyl4-hydroxybenzyl]phosphonate, m.p. 270°–75°C.

EXAMPLE 18

Barium bis[(0-ethyl)-3-acetyl-4-hydroxybenzyl]phosphonate

The same experimental procedure as that used in Examples 16 and 17 was used to treat a solution of 28 grams (0.1 mole) of sodium [(0-ethyl)-3-acetyl-4-hydroxybenzyl]phosphonate with a suspension of 12.2 grams of barium chloride dihydrate in 75 milliliters of methanol. The suspension was filtered hot after two hours of refluxing and the filtrate evaporated under reduced pressure to give 24.0 grams (73.6 percent yield) of an off-white powdery product which was identified spectroscopically as barium bis-[(0-ethyl)-3-acetyl-4-hydroxybenzyl]-phosphonate.

EXAMPLE 19

Cadmium bis[(0-ethyl)-3-acetyl-4-hydroxybenzyl]phosphonate

The same experimental procedure as that used in Examples 16 and 17 was used to react a solution of 28 grams (0.1 mole) of sodium [(0-ethyl)-3-acetyl4-hydroxybenzyl]phosphonate in 200 milliliters of methanol with 9.2 grams (0.05 mole) of cadmium chloride in 50 milliliters of methanol. A white powder weighing 24 grams (67.7 percent yield) was obtained and was identified by its infrared spectrum as cadmium bis-[(0-ethyl)-3-acetyl-4-hydroxybenzyl]phosphonate, m.p. 255°–265°C.

EXAMPLE 20

Tin bis-[(0-ethyl)-3-acetyl-4-hydroxybenzyl]phosphonate

The same experimental procedure as that used in Examples 16, 17, and 19 was used to react a solution of 29.4 grams (0.14 mole) of sodium [(0-ethyl)-3-acetyl-4-hydroxybenzyl]phosphonate in 350 milliliters of methanol with 13.4 grams (0.07 mole) of stannous chloride. After 30 minutes of heating, the slurry was filtered and the white solid material was washed with water and air dried to give 31 grams (69.7 percent yield) of a white product which was identified by spectroscopic method to be tin bis-[(0-ethyl)-3-acetyl-4-hydroxybenzyl]-phosphonate, m.p. > 300°C.

EXAMPLE 21

Di-(n-dodecyl)-3-acetyl-4-hydroxybenzyl phosphonate

The same experimental procedure as used in Examples 1, 4, 7, and 10 was used to react 58.6 grams (0.1 mole) of tri-(n-dodecyl)phosphite with 18.4 grams (0.1 mole) of 5'-chloromethyl-2'-hydroxyacetophenone. The molten mixture was kept at 150°C./0.5 mm. for 2 hours, then heated to approximately 180°C./0.5 mm. to remove dodecyl chloride. The residue was identified by its IR spectrum as di-(n-dodecyl)-3-acetyl-4-hydroxybenzyl phosphonate.

EXAMPLE 22

Sodium [(0-n-dodecyl)-3-acetyl-4-hydroxybenzyl]phosphonate

The same experimental procedure as that used in Examples 2, 5, 8, 11, and 14 was used for the preparation of the above sodium salt. The compound was identified by its infrared spectrum.

EXAMPLE 23

Nickel bis-[(0-n-dodecyl)-3-acetyl-4-hydroxybenzyl]phosphonate

The same experimental procedure as that used in Examples 3, 6, 9, 12, and 15 was used to prepare nickel bis-[(0-n-dodecyl)-3-acetyl-4-hydroxybenzyl]phosphonate. The compound was identified by its infrared spectrum.

EXAMPLE 24

Similarly by the use of trioctadecylphosphite and 5'-chloromethyl-2'-hydroxyacetophenone we obtained dioctadecyl-3-acetyl-4-hydroxybenzyl phosphonate. This compound was identified by its infrared spectrum.

EXAMPLE 25

By following the experimental procedure described in Examples 2, 5, 8, 11, and 14 we obtained sodium [(O-octadecyl)-3-acetyl-4-hydroxybenzyl]phosphonate.

EXAMPLE 26

The same experimental procedure as used in Example 23 was used to prepare nickel bis-[(O-dioctadecyl)-3-acetyl-4-hydroxybenzyl]phosphonate, which was obtained as a light green powder. Identification was made by means of its infrared spectrum.

EXAMPLE 27

Bis-2-chloroethyl)-3-acetyl-4-hydroxybenzyl phosphonate

A one-liter, four neck, round-bottom flask equipped with stirrer, condenser, thermometer, and a gas inlet tube was charged with 145.8 grams (0.789 mole) of 5'-chloromethyl-2'-hydroxyacetophenone. The flask was purged for 5–10 minutes with nitrogen while it was gently heated to 85°–90° C., at which point 212.8 grams (0.789 mole) of tris-(2-chloroethyl)phosphite was slowly introduced. Exothermicity set in and ethylene chloride distilled at 84°–85° C. After the addition was completed, the product was placed under vacuum to expel any ethylene chloride which remained entrapped in it. The product was identified by its infrared spectrum.

EXAMPLE 28

Diethyl-3-acetyl-5-bromo-4-hydroxybenzyl phosphonate

A two-liter, four neck, round-bottom flask equipped with stirrer, reflux condenser, thermometer and a dropping funnel was charged with 286.2 grams (1.0 mole) of diethyl-3-acetyl-4-hydroxybenzyl phosphonate and 500 milliliters of water. The mixture was stirred and heated at 53°–58° C. while 168 grams (1.05 mole) of bromine was introduced over a period of 2 hours. The mixture was stirred and refluxed for an additional two hours, cooled to room temperature, and the aqueous layer (upper phase) discarded. The organic layer (lower phase) was dissolved in a mixture of chloroform and ether, dried over anhydrous $MgSO_4$, filtered and concentrated under reduced pressure to give 358.5 grams (98.2 percent yield) of a reddish-yellow, viscous liquid, which was identified as diethyl-3-acetyl-5-bromo-4-hydroxybenzyl phosphonate. Anal. calculated for $C_{13}H_{18}BrO_5P$: Br, 21.88 percent. Found: Br, 21.4 percent.

EXAMPLE 29

Preparation of bis(diethyl-5-acetyl-4-hydroxy)m-xylyl phosphonate

A one-liter, four neck, round-bottom flask equipped with a stirrer, distilling head, condenser, thermometer, and a dropping funnel was charged with 116.5 grams (0.5 mole) of 3',5'-bis-chloromethyl-2'-hydroxyacetophenone [(Gazz. chim. ital. 80, 502-9(1950)] and about 10 milliliters of triethyl phosphite. The mixture was then stirred and heated to 75°–80° C. at which temperature an additional quantity of triethyl phosphite was slowly introduced into the mixture until the total quantity of the phosphite used in the reaction was equal to 166.2 grams (1.0 mole). A greenish yellow viscous liquid weighing 193.7 grams (93.5 percent yield) was obtained. The product was identified by characteristic bands in its infrared spectrum as bis(-diethyl-5-acetyl-4-hydroxy)m-xylyl phosphonate.

The compound bis(beta-chloroethyl-5-acetyl-4-hydroxy)m-xylyl phosphonate was prepared by a similar procedure as follows: One hundred and sixteen and five tenths grams (0.5 mole) of 3',5'-bis-chloromethyl-2'-hydroxyacetophenone was treated with 269.5 grams (1.0 mole) of tris-(2-chloroethyl)phosphite to give 241 grams (83.7 percent yield) of a viscous amber colored liquid identified by characteristic bands in its infrared spectrum as bis(beta-chloroethyl-5-acetyl-4-hydroxy)m-xylyl phosphonate.

EXAMPLE 30

Polypropylene resin

In this example, the effect of the various phosphonate derivatives as identified in Samples No. 2 to 18 at two concentrations on a polypropylene film was determined. Sixteen such films were prepared as follows:

Sample No. 1, which contained 100 parts unstabilized polypropylene, 0.1 part dilauryl thiodipropionate, and 1.0 part of a hindered phenol was fused in a Plasti-Corder blender at 175° for 5 minutes. The hindered phenol used was a product available under the trademark Irganox 1076, which is an alkyl ester of a carboxylic acid containing an alkylhydroxy phenyl group. This product is further identified in U.S. Pat. No. 3,330,859. The fused material was chopped and the resulting granules pressed into sheets or films about 25 mils thick using a Carver press at about 165° C.

Samples No. 2 to 18 were prepared by the same experimental procedure as used in the preparation of Sample No.1 except that the various phosphonate derivatives in the amounts indicated in Table 1 were added to each sample before fusion.

The resulting films were then used to determine the effectiveness of the phosphonate derivatives as ultraviolet light absorbers by exposing the 18 films in chambers lighted with ultraviolet light and daylight fluorescent tubes for 575 hours. Each sample was exposed so that the film protected a portion of a light-colored maple tongue blade. After 575 hours' exposure, the wood exposed directly to the light and the wood exposed behind the film of Sample No. 1 showed considerable darkening. The experiments together with the results are summarized in Table 1.

TABLE 1

Comparative effectiveness of various [(O-alkyl)-3-acetyl-4-hydroxybenzyl]phosphonates as ultraviolet light absorbers in polypropylene film after 575 hours' exposure.

| Sample No. | [(O-alkyl)-3-acetyl-4-hydroxy-benzyl]phosphonate derivative | Parts phosphonate added per 100 parts polypropylene | UV protection | Condition of film | | |
|---|---|---|---|---|---|---|
| | | | | Clarity | Color | Flexibility |
| 1 | Control | 0.0 | None | Clear | Clear | Brittle |
| 2 | Nickel bis-[(O-ethyl) . . .] | 0.5 | " | " | Sl. yellow | " |
| 3 | " | 1.0 | Very slight | " | Yellow | Cracked |

TABLE 1-continued

Comparative effectiveness of various [(O-alkyl)-3-acetyl-4-hydroxybenzyl]phosphonates as ultraviolet light absorbers in polypropylene film after 575 hours' exposure.

| Sample No. | [(O-alkyl)-3-acetyl-4-hydroxy-benzyl]phosphonate derivative | Parts phosphonate added per 100 parts polypropylene | UV protection | Clarity | Color | Flexibility |
|---|---|---|---|---|---|---|
| 4 | Tin bis-[(O-butyl) . . .] | 0.5 | Good | Opalescent | Sl. yellow | Brittle |
| 5 | " | 1.0 | Very good | " | " | " |
| 6 | Nickel bis-[(O-isooctyl) . . .] | 0.5 | Very good | Clear | " | " |
| 7 | " | 1.0 | Very slight | " | " | Cracked |
| 8 | Nickel bis-[(O-isopropyl) . . .] | 0.5 | Slight | " | " | " |
| 9 | " | 1.0 | Good | " | " | " |
| 10 | Barium bis-[(O-ethyl) . . .] | 0.5 | Slight | " | Very sl. yellow | " |
| 11 | " | 1.0 | Very good | " | Sl. yellow | Cracked less |
| 12 | Zinc bis-[(O-ethyl) . . .] | 0.5 | Slight | " | Very sl. yellow | Brittle |
| 13 | " | 1.0 | Good | " | " | " |
| 14 | Cadmium bis-[(O-ethyl) . . .] | 0.5 | Very slight | " | Sl. yellow | " |
| 15 | " | 1.0 | Slight | " | " | Cracked |
| 16 | Sodium[(O-ethyl) . . .] | 0.5 | Slight | " | Sl. tan | " |
| 17 | " | 1.0 | Very good | " | " | Sl. cracked |
| 18 | Diethyl-3-acetyl-4-hydroxybenzyl phosphonate | 1.0 | Good | " | Sl. yellow | Sl. cracked, not brittle |

The effectiveness of the compound diethyl-3-acetyl-4-hydroxybenzyl phosphonate as a fire retardant when incorporated into 60-mil thick film samples of polypropylene resin was determined according to ASTM Standard D635. In these determinations varying amounts of the phosphonate, varying amounts of Chlorowax 70, and varying amounts of a combination of the two additives were added to the resin film. Chlorowax 70 is a chlorinated paraffin containing 70 percent chlorine. The experiments together with the results are summarized in Table 2.

TABLE 2

Diethyl-3-acetyl-4-hydroxybenzyl phosphonate as a fire retardant for a polypropylene film.

| Sample No. | Concentration in percent by weight Phosphonate | Chlorowax 70 | Time in seconds to burn 4 inches | Burn time in seconds before self-extinguishing |
|---|---|---|---|---|
| 1 | 0 | 0 | 62 | ** |
| 2 | 1 | 0 | 69 | ** |
| 3 | 2.5 | 0 | 64 | ** |
| 4 | 0 | 5 | 76 | ** |
| 5 | 0 | 10 | 75 | 46 |
| 6 | 0 | 15 | 72 | 41 |
| 7 | 1 | 5 | 91 | ** |
| 8 | 1 | 10 | 90 | 20 |
| 9 | 1 | 15 | * | 6 |
| 10 | 2.5 | 5 | * | 68 |
| 11 | 2.5 | 10 | * | 5 |
| 12 | 2.5 | 15 | * | 4 |
| 13 | 5 | 10 | * | 4 |
| 14 | 5 | 15 | * | 2 |
| 15 | 7.5 | 5 | * | 60 |
| 16 | 7.5 | 10 | * | 3 |
| 17 | 7.5 | 15 | * | 3 |

*Self-extinguishing before burning 4 inches.
**Combustible

The foregoing data indicate that a combination comprising 1 to 5 percent of the phosphonate used in combination with 5 to 15 percent Chlorowax 70 is very effective as a fire retardant for polypropylene resin films.

The foregoing experiment was repeated in which a polyethylene resin film was substituted for that of the polypropylene. In this experiment, a combination comprising 3 percent phosphonate plus 10 percent Chlorowax 70 increased the time in seconds required to burn 4 inches to 233 seconds from 72 for the control.

The foregoing experiment was again repeated in which a halogenated (tetrachlorophthalic anhydride)-polyester resin film was substituted for that of the polypropylene. In this experiment, it was found that the use of Chlorowax 70 did not contribute any beneficial results. The experiments together with the results are summarized in Table 3.

TABLE 3

Diethyl-3-acetyl-4-hydroxybenzyl phosphonate as a fire retardant for a halogenated polyester resin.

| Sample No. | Concentration in percent by weight of phosphonate | Time in seconds to burn 4 inches | Burn time in seconds before self-extinguishing |
|---|---|---|---|
| 1 | 0 | 197 | ** |
| 2 | 0.5 | 213 | ** |
| 3 | 1.0 | 204 | 97 |
| 4 | 2.0 | * | 80 |
| 5 | 3.0 | * | 51 |
| 6 | 5.0 | * | 9 |
| 7 | 7.5 | * | 2 |
| 8 | 10.0 | * | 3 |
| 9 | 12.5 | * | 1.5 |
| 10 | 15 | * | 1.0 |

*Self-extinguishing before burning 4 inches.
**Combustible

EXAMPLE 31

Polyethylene resin

In this example, the effect of the various phosphonate derivatives as identified in Samples 2 to 24 on a polyethylene film was determined. Twenty-four such films were prepared as follows:

Sample No. 1 was prepared by fusing 100 parts of polyethylene in a Plasticorder blender at 175° C. for 5 minutes. The fused material was chopped and the resulting granules pressed into sheets or films about 25 mils thick using a Carver press at about 165° C.

Samples No. 2 to 24 were prepared by the same experimental procedure as used in the preparation of Sample No. 1 except that the various phosphonate derivatives in the amounts indicated in Table 4 were added to each sample before fusion.

The films were tested by exposure in a chamber lighted with ultraviolet light and daylight fluorescent tubes for a period of 575 hours. Each sample was exposed so that the film protected a portion of a light-colored maple tongue blade. After 575 hours' exposure, the wood exposed directly to the light and the wood exposed behind the film of Sample No. 1 showed considerable darkening. The experiments together with the results are summarized in Table 4.

The invention having thus been described, what is claimed and desired to be secured by Letters Patent is:

1. A compound having the formula

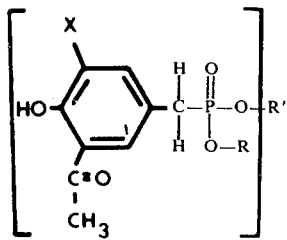

wherein R is a straight or branched chain unsubstituted or substituted alkyl group containing 1 to 18 carbon atoms wherein the substituent group is a halogen, R' is a metal selected from the group consisting of Al, Ni, Sn, and Zn, n is 2 or 3, and X is bromine or hydrogen.

2. The compound of claim 1 wherein R' is tin and n is 2.

3. The compound of claim 1 wherein R is butyl, R' is tin, X is hydrogen, and n is 2.

4. The compound of claim 1 wherein R' is zinc and n is 2.

5. The compound of claim 1 wherein R is ethyl, R' is zinc, X is hydrogen and n is 2.

6. The compound of claim 1 wherein R' is nickel and n is 2.

7. The compound of claim 1 wherein R is isopropyl, R' is nickel, X is hydrogen, and n is 2.

8. The compound of claim 1 wherein R' is aluminum and n is 3.

9. The compound of claim 1 wherein R is ethyl, R' is aluminum, X is hydrogen, and n is 3.

* * * * *